United States Patent [19]

Anninos et al.

[11] Patent Number: 5,697,883

[45] Date of Patent: Dec. 16, 1997

[54] METHOD OF INHIBITING SEIZURE ACTIVITY IN EPILEPTIC INDIVIDUALS

[76] Inventors: Photios Anninos, Ellispontou 20, Alexandroupolis, Greece; Nicolaos Tsagas, Opisthen NE. Katikies, Xanthi, Greece, 67100

[21] Appl. No.: 454,025

[22] Filed: May 30, 1995

Related U.S. Application Data

[62] Division of Ser. No. 867,201, Jun. 30, 1992, Pat. No. 5,453,072.

[30] Foreign Application Priority Data

Oct. 31, 1989 [GR] Greece ............................ 890100705

[51] Int. Cl.⁶ ............................................................ A61N 2/00
[52] U.S. Cl. ............................................................ 600/9
[58] Field of Search ........................ 600/9–15; 128/653.1, 128/897–98; 324/244, 248

[56] References Cited

U.S. PATENT DOCUMENTS 4,066,065  1/1978  Kraus ................................. 600/13
4,940,453  7/1990  Cadwell ............................ 600/13

FOREIGN PATENT DOCUMENTS 0084019   7/1983   European Pat. Off. .
0099734   2/1984   European Pat. Off. .
2370483   6/1978   France .
2707574   8/1978   Germany .
3331976   3/1985   Germany .
2156679  10/1985   United Kingdom .

OTHER PUBLICATIONS

Physics Today—vol. 39, No. 3, Mar. 1986, New York US pp. 36–44; John Clarks: "Squids, brains and gravity waves" see pp. 41–42.

Primary Examiner—John P. Lacyk
Attorney, Agent, or Firm—Dowell & Dowell

[57] ABSTRACT

A method of inhibiting seizure activity in epileptic individuals includes determining the intensity, frequency and skull coordinates of the magnetic field emitted from the epileptic focal points of an epileptic individual. The determined frequency of the magnetic field emitted from the epileptic focal points is then generated and applied to a device which emits a magnetic field, of the intensity and frequency of the magnetic fields emitted by the epileptic focal points, to the skull of the epileptic individual at the skull coordinates of each epileptic focal point.

20 Claims, 3 Drawing Sheets

METHOD OF INHIBITING SEIZURE ACTIVITY IN EPILEPTIC INDIVIDUALS

CROSS-REFERENCE TO RELATED APPLICATIONS

This is divisional of U.S. patent application Ser. No. 07/867,201, filed Jun. 30, 1992, and entitled "ELECTRONIC DEVICE FOR TREATING EPILEPTIC INDIVIDUALS", and now U.S. Pat. No. 5,453,072.

BACKGROUND OF THE INVENTION

1. Field of the Invention

The invention is directed to the treatment of central nervous system disorders and, more particularly, to a method of inhibiting seizure activity in epileptic individuals.

2. Discussion of the Related Art

The known methods of treating epileptic individuals include anticonvulsive drug treatments which smooth epileptic seizures for generalized and focal epilepsy. Such drug treatments have the disadvantage of not being capable of achieving the final cancellation of epileptic foci.

The known methods of treating epileptic individuals to finally cancel epileptic foci include neurosurgery and laser treatments. These two methods are inadequate in that they also cause other brain disorders in the individuals.

Other methods of treating epileptic individuals are known which apply strong magnetic fields of the order of $10^5$ Gauss. Magnetic fields of this magnitude can cause side effects and, accordingly, such methods are also inadequate.

To avoid having to undergo surgery and possibly incurring additional brain disorders and other side effects, most epileptic individuals have chosen to follow a drug treatment, although being only temporarily effective to inhibit the further occurrence of epileptic seizures.

Therefore, there has been a need for a method of treating epileptic individuals to permanently inhibit seizure activity which does not cause additional brain disorders or other side effects. There has further been a need for a method that is fast, painless and non-invasive, and can be performed by epileptic individuals without the assistance of other persons.

SUMMARY OF THE INVENTION

The present invention has been made in view of the above-described disadvantages of the known methods of treating epileptic individuals and has as an object to provide a method which permanently inhibits seizure activity without causing additional brain disorders and side effects.

Another object of the invention is to provide a method of inhibiting seizures in epileptic individuals which is fast, easy to administer, painless, and non-invasive.

A further object of the invention is to provide a method of inhibiting seizures in epileptic individuals which can be performed by the epileptic individuals without assistance from other persons.

Additional objects and advantages of the present invention will become apparent from the description which follows, considered in conjunction with the accompanying drawing figures, or by practice of the invention.

To achieve the objects of the invention, as embodied and broadly described herein, the method of inhibiting seizures in epileptic individuals in accordance with a preferred embodiment of the invention comprises determining the intensity, frequency and skull coordinates of the magnetic field emitted from each epileptic focal point of an epileptic individual. A low alternating voltage and substantially the same frequency as the magnetic field emitted by each epileptic focal point is generated and applied to a means for emitting a magnetic field. The emitting means emits a magnetic field to the skull of the epileptic individual at the skull coordinates of each epileptic focal point. The emitted magnetic fields are of substantially the same intensity and frequency as the magnetic fields emitted by the epileptic focal points.

DETAILED DESCRIPTION OF THE PREFERRED EMBODIMENT

Figure 1:
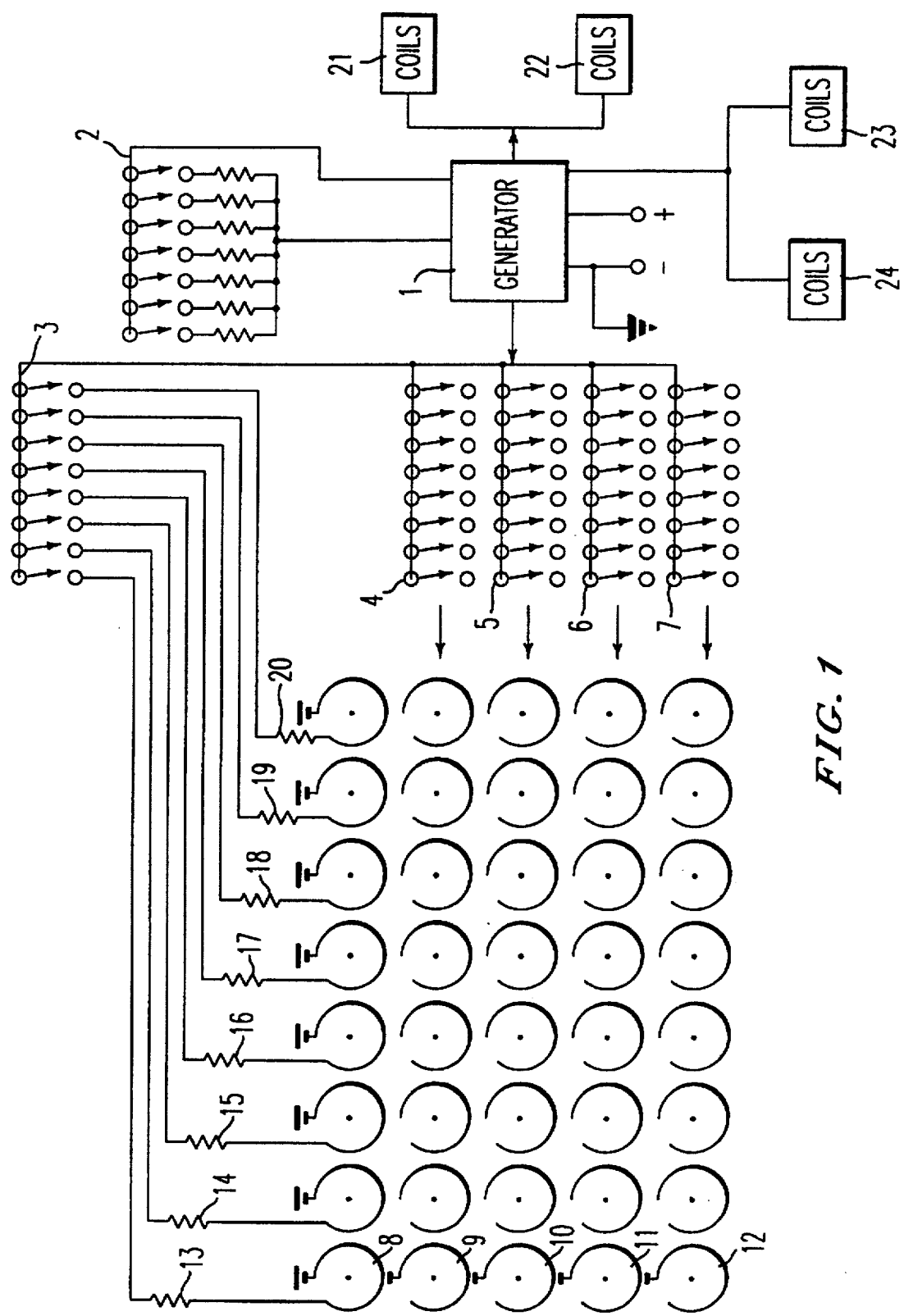
FIG. 1 illustrates an embodiment of an electronic device which is used to perform a method of treating epileptic individuals to inhibit seizure activity in accordance with a preferred embodiment of the invention.

The method of treating epileptic individuals in accordance with a preferred embodiment of the invention utilizes an electronic device as shown schematically in FIG. 1. The device comprises a generator 1, which produces a low alternating voltage and a frequency of from about 2 Hz to 7 Hz. A switch 2 is provided for selecting the operative frequency of the generator, and additional switches 3, 4, 5, 6 and 7 are provided for selecting the specific coils to which to supply the selected frequency. The coils are arranged in rows 8, 9, 10, 11 and 12, and may be in similar additional groups of coils 21, 22, 23 and 24. Resistors 13, 14, 15, 16, 17, 18, 19 and 20 are disposed between the coils of the rows 8, 9, 10, 11 and 12 and the switches 4, 5, 6 and 7. Similar resistors (not shown) are associated with the other groups of coils 21, 22, 23 and 24.

Figure 2:
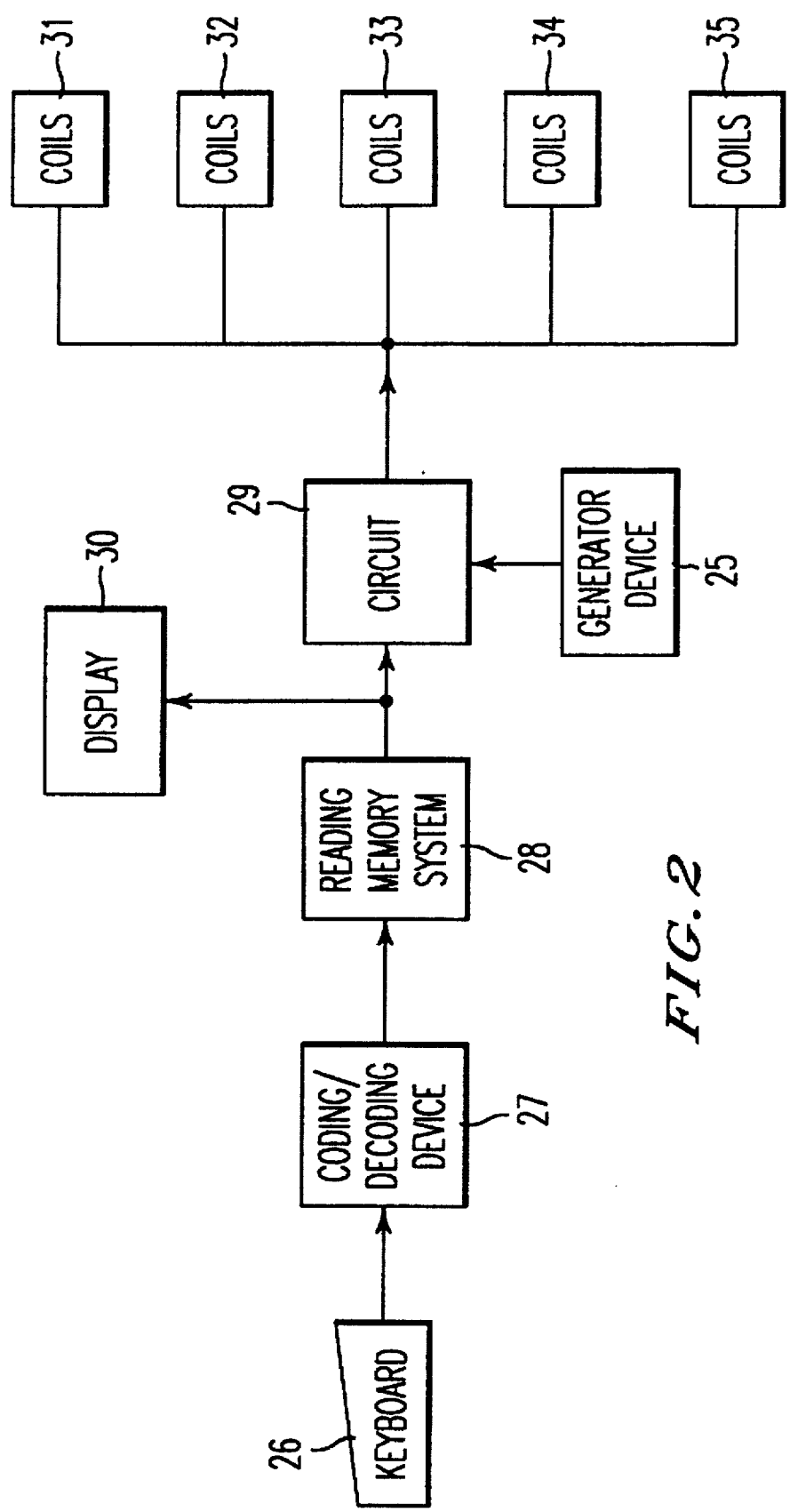
FIG. 2 illustrates another embodiment of the device which is used to perform the method in accordance with preferred embodiment of the invention.

Referring to FIG. 2, the electronic device may optionally comprise a plurality of generators, which each produce a low alternating voltage and a specific frequency. For example, the illustrated generator device 25 includes seven separate generators. The plurality of generators can simultaneously supply a number of coils in order to produce alternating magnetic fields. The generators are each adapted to produce a low alternating voltage, and a frequency from 2 Hz to 7 Hz.

A key board 26 is provided to enable an operator to select the specific generator(s) and coils 26 to be activated.

The device further comprises a code maker/decode maker 27, a reading memory system 28, a display screen 30, a combinatory circuit 29, and one group of coils arranged in rows 31, or similar additional groups of coils 32, 33, 34 and 35. The coils of the different groups 31, 32, 33, 34 and 35 are connected to the circuit 29 via resistors (not shown).

The coils produce a magnetic pulse which may have a square (symmetrical or non-symmetrical), triangular, sinusoidal or saw-like wave form. The coils may also produce a combination of these pulse forms.

The number of coils, the cross-section of the coil turns, and the shape and composition of the cores, can be varied. The perpendicular cross-section of the coils is substantially circular and the number of turns of the coils is relatively small. The coils have a small diameter of about one centimeter and are enclosed between two parallel plane surfaces (not shown) such that the axes of the coils are perpendicular to the plane surfaces. The wires of the coils are composed of materials having good conductivity such as silver, copper and the like. The cores are composed of plastic, ferrite and other materials having a suitable magnetic permeability.

The method in accordance with the invention is useful to treat epileptic convulsions in epileptic patients being treated by a drug treatment and receiving anticonvulsion medication. As explained above, such drug treatments are only temporarily effective and must be repeatedly administered, while the present method permanently inhibits seizure activity.

The time required to perform the method varies for individual patients, and depends on the size of the epileptic foci. In general, a greater amount of time is required to treat patients having deeper foci. The method is sufficiently easy to perform, such that it can be performed by a patient having a personal device without the assistance of others. In such cases, the personal device is initially calibrated using a device that measures the characteristics of the epileptic foci, and any other brain disorders the patient might have. Without the initial calibration, individuals are unable to locate the electronic device on their skull without assistance because the device can disorganize other regions of their brain. The individual can self-administer the treatment when certain characteristic signs of oncoming seizures are felt or sensed, for example, by smell or taste.

In accordance with the invention, the characteristics of the epileptic foci of an epileptic individual are initially determined by a superconducting quantum interference device, or "SQUID". The SQUID gives the precise coordinates of the epileptic foci, as well as the intensity and frequency of the magnetic fields which are emitted from the epileptic foci. The epileptic foci characteristics are specific for each epileptic individual. SQUID apparatuses are described in detail in the following publications of the present inventors: P. A. Anninos and N. F. Tsagas: *Brain Research Bulletin*, Vol. 16, 1986; and *International Journal of Neuroscience*, Vol. 37, 1987.

The effectiveness of the method of the invention is based on the proper use of the SQUID, at least for the first smoothing of the patient during which the first calibration of the electronic device is performed. The SQUID includes a probe which is maintained a selected distance from the individual's skull so that relative contact does not occur. For each cerebral hemisphere of an individual, the probe is used to take measurements at thirty-two separate points. The points are 1.5 cm from each other, about one-half of the SQUID sensor diameter, to avoid magnetic overlapping between nearby points. The points form a matrix of a rectangular shape and are located as defined by the International 10–20 Electrode Placement System. The reference points are designated T3, T4, P3, P4, F3, F4 for the left or right temporal hemisphere, the occipital hemisphere, and the frontal brain region. The points are located with a self-adhesive paper on a plastic hat, which is placed on the patient's head prior to locating the reference points. The points are located at perfectly defined positions on the skull, provided that the coordinates of the reference points have been defined. Knowledge of the coordinates of the reference points also gives the coordinates of the thirty-two points, and the coordinates of the epileptic foci.

Figure 3A:
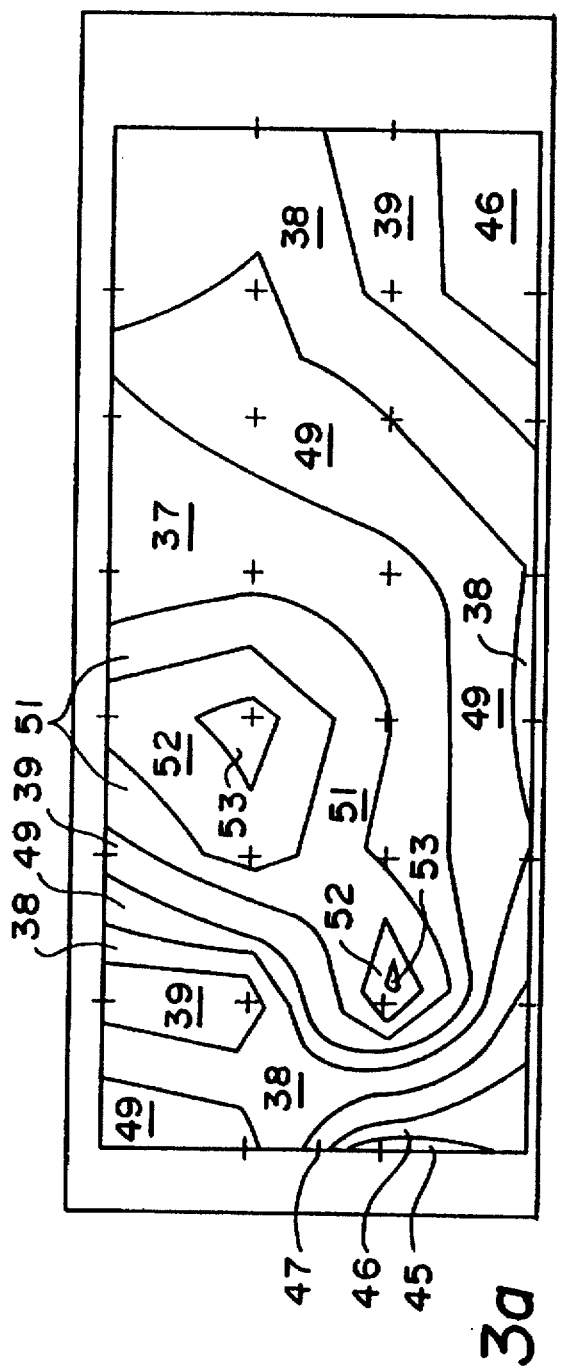
FIG. 3a illustrates an isospectral map produced from measurements made by a SQUID of the left temporal region of an epileptic individual before being treated by the method in accordance with the invention.
Figure 3B:
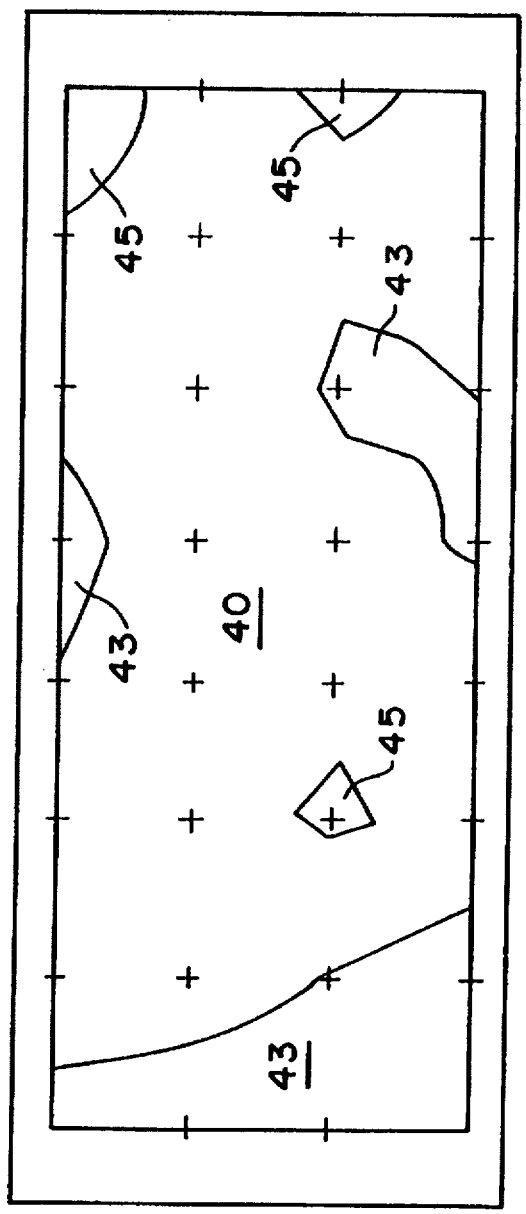
FIG. 3b illustrates an isospectral map produced from measurements made by a SQUID of the same region of the brain as in FIG. 3a after being treated by the method in accordance with the invention.

Next, the probe sensor of the SQUID is located 3 mm above each point and thirty-two consecutive measurements, each of a one second duration, are taken at a sampling frequency of 256 Hz. The measurements are analyzed using Fourier statistical analysis, and the spatial distribution of the amplitude of the Fourier power spectrum for a specific frequency, or for a frequency range, is determined. Using an electronic computer; all equal power spectra amplitudes for a given frequency or frequency range, are connected to obtain maps of ISO-Spectral Amplitudes (ISO-SA maps) as depicted in FIGS. 3a and 3b. If epileptic foci are present, their coordinates and intensity are obtained from the maps and from the power spectrum density. FIG. 3a illustrates the location and power of several epileptic foci 36, 37, 38 as measured prior to treatment with the present method. Finally, after the epileptic foci are identified using spectral analysis, the frequency of the magnetic fields emitted from the foci are found.

After the characteristics of the epileptic foci are determined as described above, the coils of the electronic device illustrated in FIG. 1 or FIG. 2 are positioned so that the alternating magnetic fields emitted by the coils are parallel to the alternating magnetic fields emitted from the neuronal generators of the epileptic foci. That is, the surfaces of the coils are applied simultaneously and parallel to the projected epileptic foci on the skull, or at another part of the central nervous system.

The generator (or plurality of generators) is activated to produce a low alternating voltage which is applied to the ends of the selected coils. The coils produce a current of the same frequency as the generator, and the magnetic field emitted by the coils is also of the same frequency. The power and frequency of the emitted magnetic fields are of the same order of magnitude as those emitted from the epileptic foci. More particularly, the electronic device produces alternating magnetic fields of a low frequency of about 2 to 7 Hz. The magnetic fields also have a low intensity of $10^{-4}$ to $10^{-8}$ Gauss, which is $1/10^4$ or $1/10^8$ of the intensity of the earth's magnetic field. Consequently, the magnetic fields emitted by the coils do not cause side effects as do the known methods which apply a much stronger magnetic field. Therefore, the method in accordance with the invention is safe to administer.

A further advantage of the present method is that it takes only several minutes each time the device is applied to the epileptic foci. The smoothing treatment lasts for several days or months.

The following TABLE I gives the ISO-SA map region number and the corresponding MEG amplitude for FIGS. 3a and 3b.

TABLE I

| ISO-SA Map Region Number | MEG Amplitude (ft/√Hz) |
|---|---|
| 42 | <200 |
| 43 | <400 |
| 40 | <600 |
| 45 | <800 |
| 46 | <1000 |
| 39 | <1200 |
| 38 | <1400 |
| 49 | <1600 |
| 37 | <1800 |
| 51 | <2000 |
| 52 | <2200 |
| 36 | >2200 |

FIG. 3a is an ISO-SA map of the left temporal region of an epileptic individual before being treated by the method in accordance with the invention. The measurements used to create the map were provided by a SQUID. Epileptic foci 37, 38 and 39 are shown, having corresponding power amplitudes below 1800 ft/√Hz, below 1400 ft/√Hz and below 1200 ft/√Hz, respectively.

FIG. 3b is an ISO-SA map of the same region of the same individual as represented by FIG. 3a, produced from measurements made by a SQUID after the individual was treated by the method in accordance with the invention. As shown in the region 40, the epileptic foci 36, 37, 38 and 39 were no longer present following the treatment. The isospectral amplitudes of the regions of the map where the foci 36, 37, 38 and 39 previously existed are below 800 FT/√Hz, as shown in the region 40, and accordingly the foci were considered to have been cancelled.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims, and their equivalents.

What is claimed is:

1. A method of inhibiting seizure activity in epileptic individuals, comprising the steps of:
   determining skull coordinates, intensity and frequency of the magnetic field emitted from epileptic focal points of an epileptic individual;
   generating a low alternating voltage at substantially the same frequency as the magnetic field emitted from said epileptic focal points;
   applying the generated voltage and frequency to an emitting means for emitting a magnetic field; and
   emitting a magnetic field from said emitting means to the skull of the epileptic individual at the skull coordinates of each epileptic focal point, the emitted magnetic fields being of substantially the same intensity and frequency as the magnetic fields emitted by the epileptic focal points.

2. The method of claim 1, wherein the step of determining comprises measuring the emitted magnetic field intensity, for a frequency range, of each epileptic focal point using a SQUID.

3. The method of claim 2, wherein the SQUID comprises a probe and the step of determining comprises positioning the probe a distance from the scalp of the epileptic individual and taking a reading of the intensity of the magnetic field emitted from the scalp at a plurality of spaced points.

4. The method of claim 3, wherein the points are spaced from each other an effective distance to prevent magnetic overlapping between the readings.

5. The method of claim 4, wherein the readings are taken for each cerebral hemisphere at a plurality of equally spaced locations.

6. The method of claim 4, wherein the step of determining comprises analyzing the readings to determine the spatial distribution over the scalp of the amplitude of the power spectrum for said frequency range, and forming maps of readings of equal power amplitude to determine the intensity, frequency and skull coordinates of the epileptic focal points.

7. The method of claim 6, wherein the generated frequency is from about 2 Hz to 7 Hz.

8. The method of claim 7, wherein the step of generating comprises providing a plurality of generators, each of which produces an alternating low voltage and a frequency of from about 2 Hz to 7 Hz.

9. The method of claim 1, wherein said emitting means emits a magnetic field substantially parallel to the magnetic fields produced by the epileptic focal points.

10. The method of claim 9, wherein said emitting means comprises a plurality of coils and the step of emitting comprises selecting a number of coils to emit magnetic fields.

11. The method of claim 10, wherein said coils each emit a magnetic field of a frequency of from about 2 Hz to 7 Hz.

12. A method of inhibiting seizure activity in epileptic individuals, comprising the steps of:
   measuring the intensity and frequency of the magnetic field emitted from the scalp of an epileptic individual at a plurality of spaced points using a SQUID;
   analyzing the intensity measurements to determine the spatial distribution over the scalp of the amplitude of the power spectrum for a frequency range;
   forming a map of readings of equal power amplitude for said frequency range to determine the intensity, frequency and skull coordinates of the epileptic focal points;
   generating a low alternating voltage at substantially the same frequency as the magnetic field emitted from each epileptic focal point;
   applying the generated low alternating voltage and frequency to an emitting means for emitting a magnetic field; and
   emitting a magnetic field from said emitting means to the skull of the epileptic individual at the skull coordinates of each epileptic focal point and substantially parallel to the magnetic fields produced by the epileptic focal points, the emitted magnetic fields being of substantially the same intensity and frequency as the magnetic fields emitted by the epileptic focal points.

13. The method of claim 12, wherein the SQUID comprises a probe and the step of measuring comprises positioning the probe a distance from the scalp of the epileptic individual and measuring the intensity of the magnetic field emitted from the scalp at a plurality of spaced points.

14. The method of claim 13, wherein the points are spaced from each other an effective distance to prevent magnetic overlapping between the points.

15. The method of claim 14, wherein the readings are taken for each cerebral hemisphere at a plurality of equally spaced locations.

16. The method of claim 14, wherein the generated frequency is from about 2 Hz to 7 Hz.

17. The method of claim 16, wherein the step of generating comprises providing a plurality of generators, each of which produces an alternating voltage and a frequency of about 2 Hz to 7 Hz.

18. The method of claim 17, wherein the emitting means comprises a group of coils having a plurality of rows of coils, and each of the rows of coils includes a plurality of coils, and the step of emitting includes selecting a number of coils to emit magnetic fields.

19. The method of claim 18, wherein each of said number of coils selected emits a magnetic field of a frequency of about 2 Hz to 7 Hz.

20. A method of inhibiting seizure activity in epileptic individuals, comprising the steps of:
   measuring the intensity of the magnetic field emitted from the scalp of an epileptic individual, for a frequency range, at a plurality of spaced points using a SQUID;
   analyzing the intensity measurements to determine the spatial distribution over the scalp of the amplitude of the power spectrum for a frequency range, and forming a map of readings of equal power amplitude for said frequency range to determine the intensity, frequency and skull coordinates of the epileptic focal points;

providing a plurality of coils;

generating a low alternating voltage at a frequency of from about 2 Hz to 7 Hz;

applying the generated voltage and frequency to a selected number of said plurality of coils; and emitting a magnetic field from the selected coils to the skull of the epileptic individual at the skull coordinates of each epileptic focal point and substantially parallel to the magnetic fields produced by the epileptic focal points, the emitted magnetic fields being of substantially the same intensity and frequency as the magnetic fields emitted by the epileptic focal points.

* * * * *